United States Patent [19]
Dolan et al.

[11] Patent Number: 5,607,050
[45] Date of Patent: Mar. 4, 1997

[54] VIAL FLOSS DISPENSER

[75] Inventors: John W. Dolan, Boothwyn, Pa.; John W. Spencer, Jr., Rising Sun; Rickey I. Hill, Elkton, both of Md.; David D. McClanahan, Harleysville, Pa.

[73] Assignee: W. L. Gore & Associates, Inc., Newark, Del.

[21] Appl. No.: 551,503

[22] Filed: Nov. 1, 1995

[51] Int. Cl.$^6$ .............................. B65H 1/00; A61C 15/00
[52] U.S. Cl. ........................ 206/63.5; 206/368; 206/408; 132/325
[58] Field of Search ................................ 206/63.5, 459.5, 206/368, 407–409; 132/323–329

[56] References Cited

U.S. PATENT DOCUMENTS

| | | |
|---|---|---|
| D. 271,431 | 11/1983 | Seelig . |
| D. 339,215 | 9/1993 | Spencer, Jr. . |
| D. 339,426 | 9/1993 | Spencer, Jr. . |
| 817,050 | 4/1906 | De La Cour . |
| 1,454,429 | 5/1923 | Dresser .................................. 132/325 |
| 2,340,184 | 1/1944 | Gray . |
| 2,853,082 | 9/1958 | Nelson .................................. 132/326 |
| 2,929,541 | 3/1960 | Castelli et al. . |
| 3,246,815 | 4/1966 | Aronson . |
| 3,480,190 | 11/1969 | Freedman . |
| 3,890,986 | 6/1975 | Gerlich .................................. 206/63.5 |
| 4,111,089 | 9/1978 | Montaruli . |
| 4,162,688 | 7/1979 | Tarrson et al. . |
| 4,546,782 | 10/1985 | Kucher .................................. 132/328 |
| 4,706,843 | 11/1987 | Thornton .................................. 206/389 |
| 4,796,783 | 1/1989 | Paulson .................................. 132/325 |
| 4,934,389 | 6/1990 | Pettiford . |
| 5,076,302 | 12/1991 | Chari . |
| 5,156,311 | 10/1992 | Spencer, Jr. et al. . |

FOREIGN PATENT DOCUMENTS

91/13594   9/1991   WIPO .

*Primary Examiner*—Paul T. Sewell
*Assistant Examiner*—Luan K. Bui
*Attorney, Agent, or Firm*—Victor M. Genco, Jr.

[57] ABSTRACT

A floss dispenser has an essentially cylindrical case, the case including a cylindrical wall with an inner surface and two opposite ends. The case further includes an opening formed in at least one end for receiving a spool having floss wrapped around a hub. A cap is received within the opening in the end of the case. The cap has an annular wall for receiving and centering the hub of the spool when the cap is sealing the opening of the case, and at least one opening formed therein through which floss is threaded out of the end of the case. For securely attaching the cap to the case, a first interlocking engagement member associated with the cap engages a mating second interlocking engagement member associated with the case. The arrangement is such that upon insertion of the cap into the open end of the case and rotating the cap, the first engagement member of the cap engages the second engagement member of the case for preventing the axial movement of the cap relative to the case. Preferably, the first engagement member includes three protrusions which engage three mating protrusions of the second engagement member for securing the cap to the case.

10 Claims, 4 Drawing Sheets

VIAL FLOSS DISPENSER

FIELD OF THE INVENTION

This invention generally relates to containers for holding and dispensing dental floss material. More particularly, the present invention relates to a substantially cylindrical, vial-shaped dental floss dispenser.

BACKGROUND OF THE INVENTION

Dental floss is dispensed from a wide variety of containers and dispensers. Most common floss dispensers are available in a rectangular package having a sideways mounted, circular spool of floss material which dispenses the dental floss through a hole formed in the top of the package past a cutting blade. The top of the package and the cutting blade are generally protected by a hinged lid as is well-known in the prior art. A particular successful example of this basic design, which is taught in U.S. Pat. Nos. 5,156,311, and D-339,426, includes a view-window through which the amount of floss in the container can be monitored. Since floss is dispensed from these containers in a direction perpendicular to the axis of the floss spool, floss generally dispenses very smoothly.

One shortcoming with this basic design is limited holding capacity of the container. While such packages can readily hold 50 to 75 yards of floss fiber, a significant increase in the amount of floss above this volume requires a redesign of the container. When W. L. Gore & Associates, Inc., of Flagstaff, Ariz., introduced a floss package holding 200 yards of material, it opted for a cylindrical vial, with floss mounted on an upright spool loosely inserted within the cylindrical container. While it would be preferred to dispense the floss from the top of such a container (i.e., in a direction approximately parallel to the axis of the spool), it was discovered that the floss would not cleanly pay off the spool when the floss was fed through a hole in the top of the vial, becoming periodically tangled and jammed during pay off.

To solve this pay off problem, the container was designed to support the spool of floss in a centered position with the spool's top end mating with a unique cap on the end of the container. This cap was designed to include a recess in its center into which a projection from the spool seats while remaining free to spin around its axis. An annular groove around the recess in the cap allows floss to spin off the spool and through an opening in the cap. For attaching the cap to the container, the cap was designed with a snap fit attachment which mates with a formation on the inner wall of the container.

However, one shortcoming of this design is that the cap was sometimes too difficult to remove from the container and therefore not readily adapted for replacing the spool of floss should it become depleted. One easy solution was to make the cap removable from the container in an easy fashion. However, when the cap is not securely attached to the cylindrical container, it oftentimes is subject to unwanted removal therefrom when dispensing floss through the cap in the manner described above. The secure attachment of the cap to the container ensures that the spool is securely held within the container when removing floss from the spool whereby axial forces are applied to the spool and transferred to the cap.

The foregoing illustrates limitations known to exist in present floss dispensers. Thus, it is apparent that it would be advantageous to provide an improved floss dispenser directed to overcoming one or more of the limitations set forth above. Accordingly, a suitable alternative is provided including features more fully disclosed hereinafter.

SUMMARY OF THE INVENTION

The present invention advances the art of dental floss dispensers, and the techniques for creating such floss dispensers, beyond which is known to date. In one aspect of the present invention a floss dispenser comprises an essentially cylindrical case, the case including a cylindrical wall with an inner surface and two opposite ends. The case has an opening formed in at least one end for receiving a spool having floss wrapped around a hub. A cap is adapted to be received within the opening in the end of the case. The cap has means for receiving and centering the hub of the spool when the cap is sealing the opening of the case, and at least one opening therein through which floss is threaded out of the end of the case. The improvement of the present invention comprises means for securely attaching the cap to the case comprising a first interlocking engagement member associated with the cap and a mating second interlocking engagement member associated with the case. The arrangement is such that upon insertion of the cap into the open end of the case and rotation the cap, the first engagement member of the cap engages the second engagement member of the case for preventing the axial movement of the cap relative to the case.

More particularly, the first engagement member comprises at least one (and preferably three) radially outwardly extending, circumferential protrusion formed on the wall portion of the cap, and the second engagement member comprises at least one (and preferably three) radially inwardly extending, circumferential protrusion formed on the inner surface of the cylindrical wall of the case. The protrusion of the cap is adapted to engage the protrusion of the case when attaching the cap to the case. The protrusion of the cap has an engaging surface which faces a mating engaging surface of the protrusion of the case when in engagement therewith. The second engagement member of the case further comprises a stop post formed on the inner wall of the case. The stop post extends radially inwardly and in a direction generally transverse to the direction of the second circumferential protrusion of the cylindrical wall of the case. The stop post engages the first circumferential protrusion of the cap when rotating the cap to its attached position and defines a limit for rotating the cap. The second engagement member of the case further comprises an interposed detent element which extends radially inwardly and in a direction generally parallel to the stop post.

It is, therefore, a purpose of the present invention to provide a floss dispenser with the large capacity of a vial but with ready pay off of the floss material.

It is another purpose of the present invention to provide a vial-type floss dispenser that can dispense floss through one of its ends without tangling or jamming.

It is still another purpose of the present invention to provide a vial-type floss dispenser that can dispense floss through one of its ends so that the end, as well as the exposed floss and the cutting blade, can be protected with a removable lid between uses.

It is further a purpose of the present invention to provide a vial-type floss dispenser having a cap which is securely attached to a container of the dispenser and can be removed to access, remove and/or replace a depleted spool of floss.

It is yet another purpose to provide a vial-type floss dispenser having a removable cap or lid designed such that the cap can only be arranged in one predetermined orientation when operatively positioned on the floss dispenser.

It is yet another advantage of the present invention to provide for a stabilization seat rim for the floss spool to help minimize the tangling of dental floss around the bottom protrusion of the floss spool.

Additionally, the stabilization seat is transparent so that the user can readily identify the quantity of floss contained on the spool.

These and other purposes of the present invention will become evident from review of the following specification.

BRIEF DESCRIPTION OF THE DRAWINGS

The foregoing summary, as well as the following detailed description of a preferred embodiment of the invention, will be better understood when read in conjunction with the appended drawings. For purposes of illustrating the invention, there is shown in the drawings an embodiment which is presently preferred. It should be understood, however, that the invention is not limited to the precise arrangement and instrumentality shown. In the drawings.

DETAILED DESCRIPTION OF THE INVENTION

Figure 1:
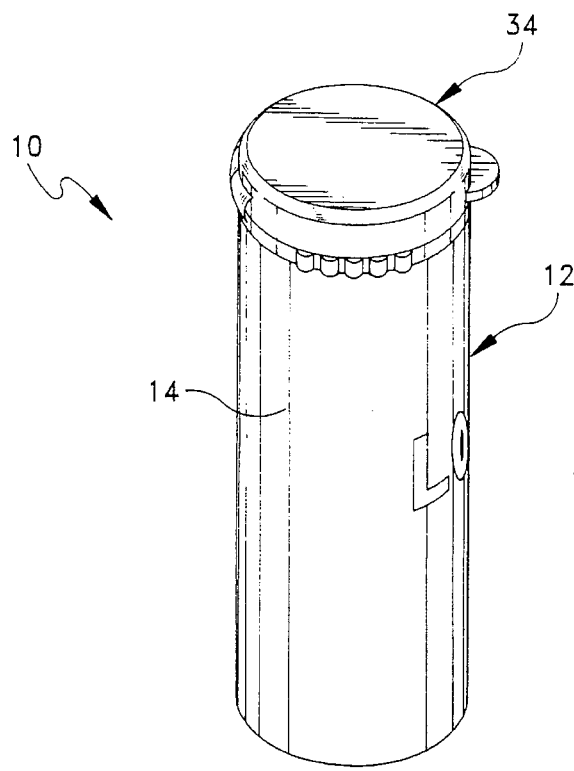
FIG. 1 is a front perspective view of a dental floss dispenser of the present invention.

Referring now to the drawings, wherein similar reference characters designate corresponding parts throughout the several views, the improved dental floss dispenser of the present invention is generally illustrated at 10 in FIGS. 1–7. The dispenser 10 comprises a cylindrical vial case, generally indicated at 12, having a cylindrical wall 14 with a first open end 16 and a second open end 18 closed by an end plug 20 which is snap fitted to the case 12 in the manner illustrated in FIG. 7.

Inserted within the case 12 is a spool generally indicated at 22 having a hub 24 around which is wrapped a length of dental floss 26. The spool 22 is mounted with its axial hub 24 coaxial with the longitudinal axis A of the container (see FIG. 4). The hub 24 extends beyond the dental floss 26 on either end, thereby forming a lower projection 28 and an upper projection 30. The lower projection 28 of the spool hub 24 is received within a circular formation 32 formed in the end plug 20 (see FIG. 7).

Figure 2:
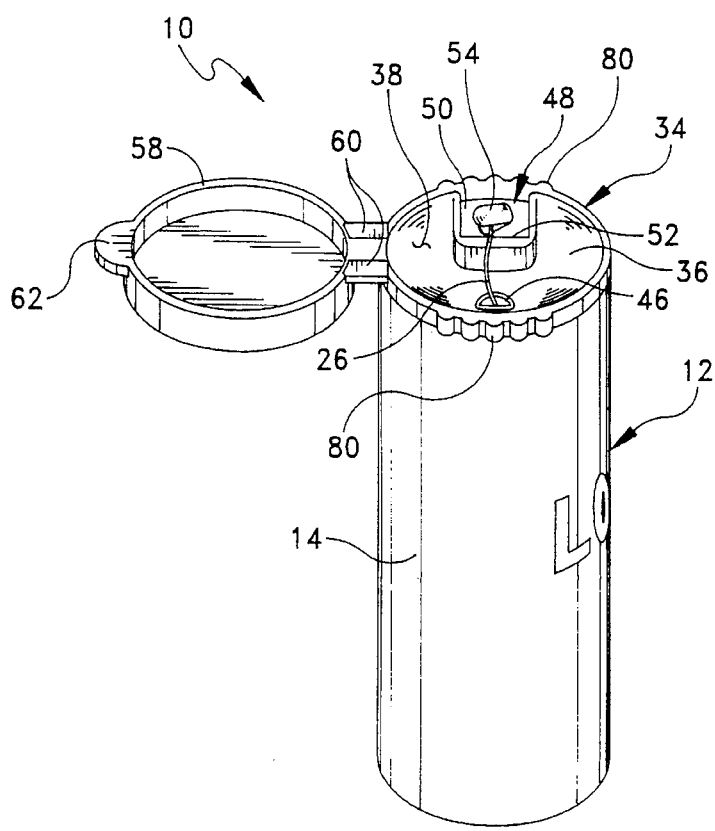
FIG. 2 is a front perspective view of the dental floss dispenser illustrating a lid of the dispenser in an open position.
Figure 3:
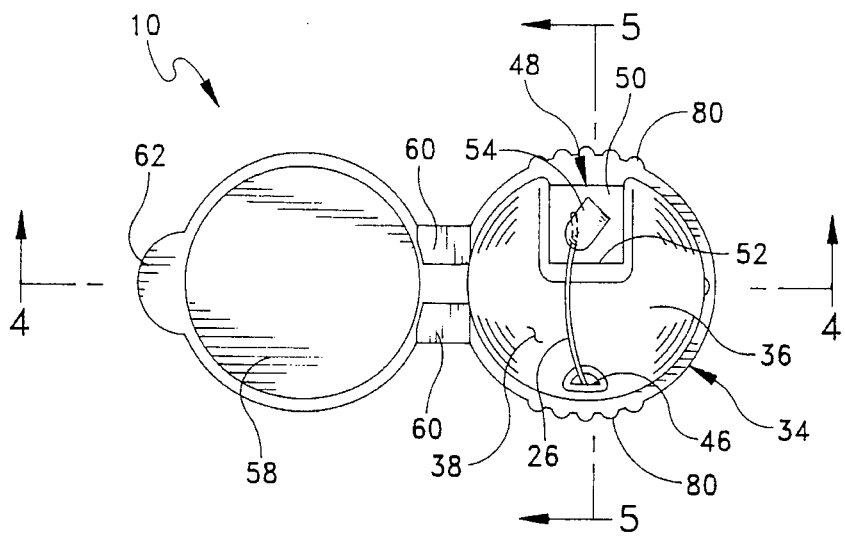
FIG. 3 is a top plan view of the dispenser depicted in FIG. 2.
Figure 4:
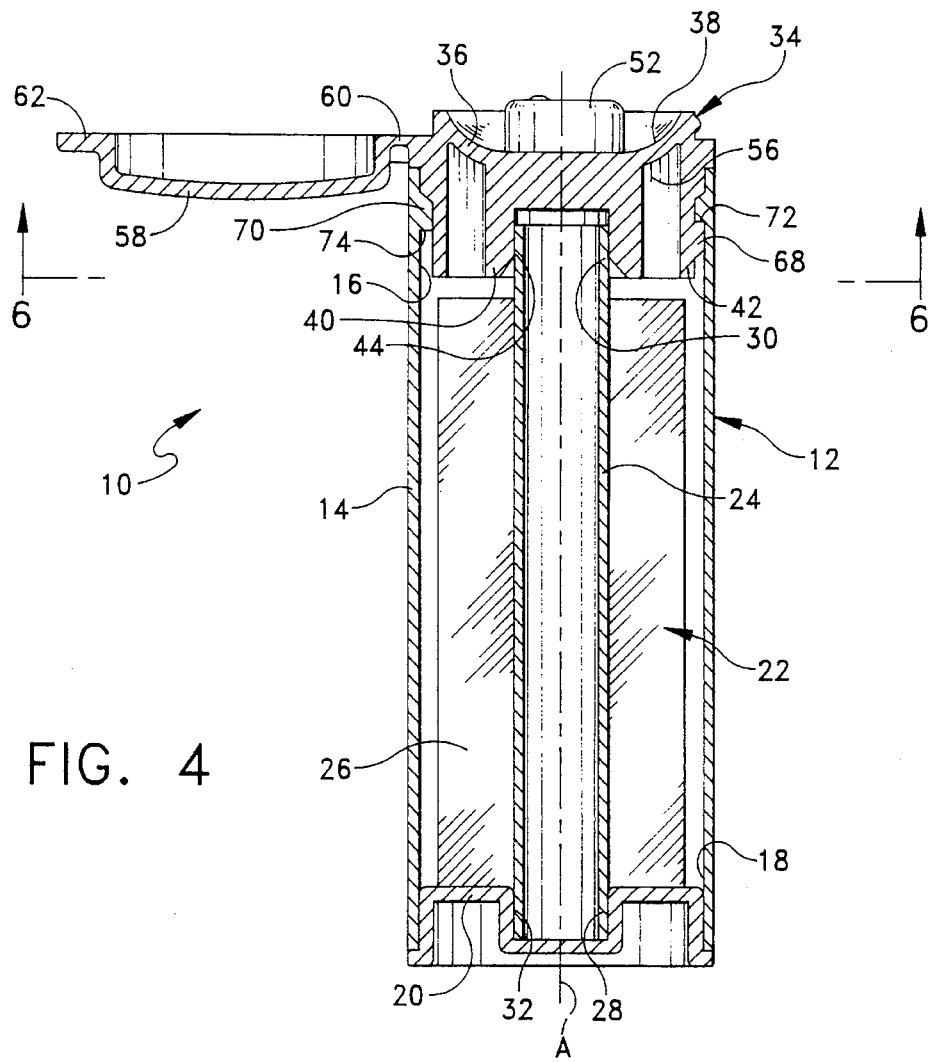
FIG. 4 is a cross-sectional view taken along line 4—4 of FIG. 3.
Figure 7:
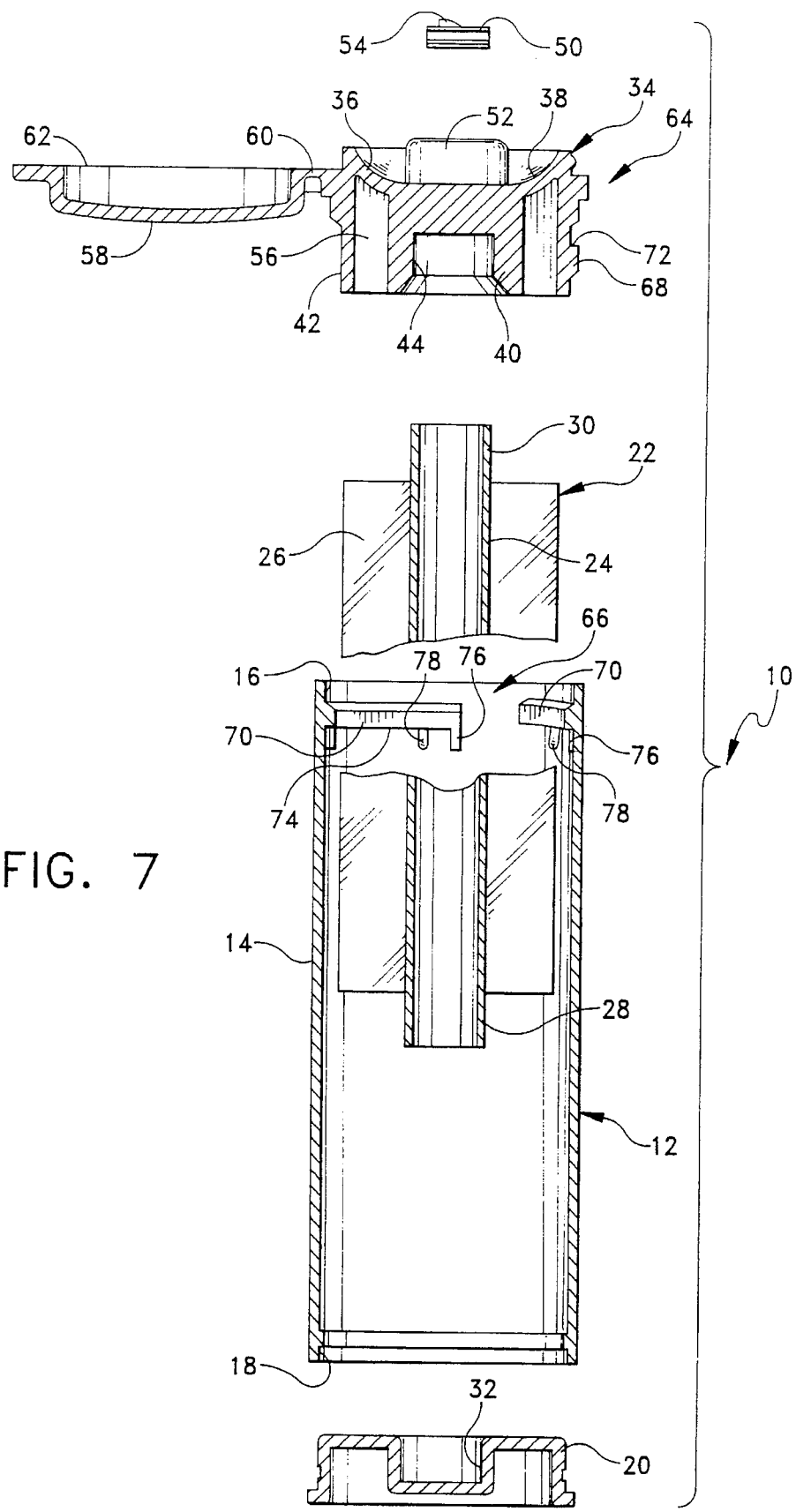
FIG. 7 is an exploded, elevational partial cross-sectional view of the floss dispenser.

Referring now to FIGS. 2–5 and 7, the first open end 16 of the case 12 is sealed with a cap which is generally indicated at 34. As illustrated in FIG. 7, the cap 34 is removable from the case 12 so as to provide access to the interior of the dispenser 10. Turning to FIG. 4, the cap 34 has an arcuate wall 36 with an upwardly-facing surface 38, an inner, downwardly extending annular wall 40 which receives the upper projection 30 of the spool hub 24 therein for centering the hub 24 when the cap 34 is inserted within the opening 16 of the case 12, and an outer, downwardly extending annular wall 42 which engages the cylindrical wall 14 of the case 12. The inner annular wall 40, which is broadly referred to as "receiving and centering means", has a snug fit with the upper projection 30 of the spool hub 24, but allows the spool to axially rotate so as to pay out floss 26. More particularly, there is another circular formation 44 formed interiorly of the inner annular wall 40 which receives the upper projection 30 of the hub 24 when the cap 34 is mounted on the case 12. The formation 44 is proportioned to provide a close yet unrestrained retention of the projection 30 in such a manner that the spool 22 will spin freely within the cap 34 as floss 26 is dispensed therefrom.

As shown in FIGS. 2 and 3, there is an opening 46 formed in the arcuate wall 36 through which dental floss 26 is threaded out of the first end 16 of the case 12. A blade assembly generally indicated at 48 is attached to the arcuate wall 36 of the cap 34 for assisting the user of the dispenser 10 to remove a length of floss therefrom. The blade assembly 48 comprises a clip 50 which slides into a pre-cut slot 52 in the arcuate wall 36 of the cap 34, and a raised cutting edge or blade 54 around which floss 26 is severed. In the preferred embodiment, the cutting blade 54 is oriented on the opposite side of the cap 34 from the opening 46. This spaced apart relationship provides an exposed segment of floss 26 (or leader) that can be grasped by the user. It is particularly preferable that at least a portion of the cap 34 be fabricated from transparent material, such as plastic or glass, so that the floss 26 wrapped around the spool hub 24 can be seen through the top of the dispenser 10. This provides an easy method for a user to determine the amount of floss 26 left within the dispenser 10. Alternatively, the end plug 20 may be transparent for accomplishing this purpose.

There is an annular groove 56 positioned between the inner and outer annular walls 40, 42. This groove 56 provides sufficient space to allow floss 26 dispensing from the spool hub 24 to pass freely upwardly through the opening 46 in the cap 34. It has been determined that floss 26 will dispense very readily through the opening 46 when the spool hub 24 is retained in the manner described above. The positioning of the spool 22 vertically within the case 12 with the floss 26 dispensing off the spool hub 24 and upwardly through the annular groove 56 and into the opening 46 avoids the jamming problems previously encountered with top dispense vial floss dispensers where the floss spool is not maintained in a consistent, centered spinning orientation. As a result, the floss dispenser 10 of the present invention provides a smooth, unencumbered floss pay off through its opening 46 in the cap 34.

Also illustrated in FIGS. 1–4, the cap 34 includes a lid 58 which is hingedly connected to the cap 34 by a pair of hinge elements 60, and movable from a closed position (FIG. 1) to an open position (FIG. 2). The lid 58 completely seals over the entire top surface 38 of the cap 34 between uses, thoroughly sealing the opening 46, the exposed segment of floss 26, and the blade assembly 48. The lid 58 may also comprise a thumb tab 62 for assisting the user in hingedly moving the lid 58. Preferably, the lid 58 is aligned in such a manner that it hingedly moves away from, and is centered with, a logo or other printed indicia provided on the outer surface of the cylindrical wall 14 of the case 12.

As has been explained, one shortcoming of this design is that the cap 34 is sometimes too difficult to remove from the case 12, and therefore is not readily adapted for replacing the spool of floss 22 should it become depleted. However, if the cap 34 is not securely attached to the cylindrical case 12, it may be subject to unwanted removal from the case 12. An improvement of the present invention lies in a means provided for securely attaching the cap 34 to the case 12. More particularly, the cap 34 includes a first interlocking engagement member, generally indicated at 64, which mates with a second interlocking engagement member, generally indicated at 66, of the case 12 (see FIG. 7). The arrangement is such that the cap 34 can only be arranged in one predetermined orientation with respect to the case 12 when the cap 34 is operatively inserted into the first open end 16, and the first engagement member 64 of the cap 34 engages the second engagement member 66 of the case 12.

Figure 5:
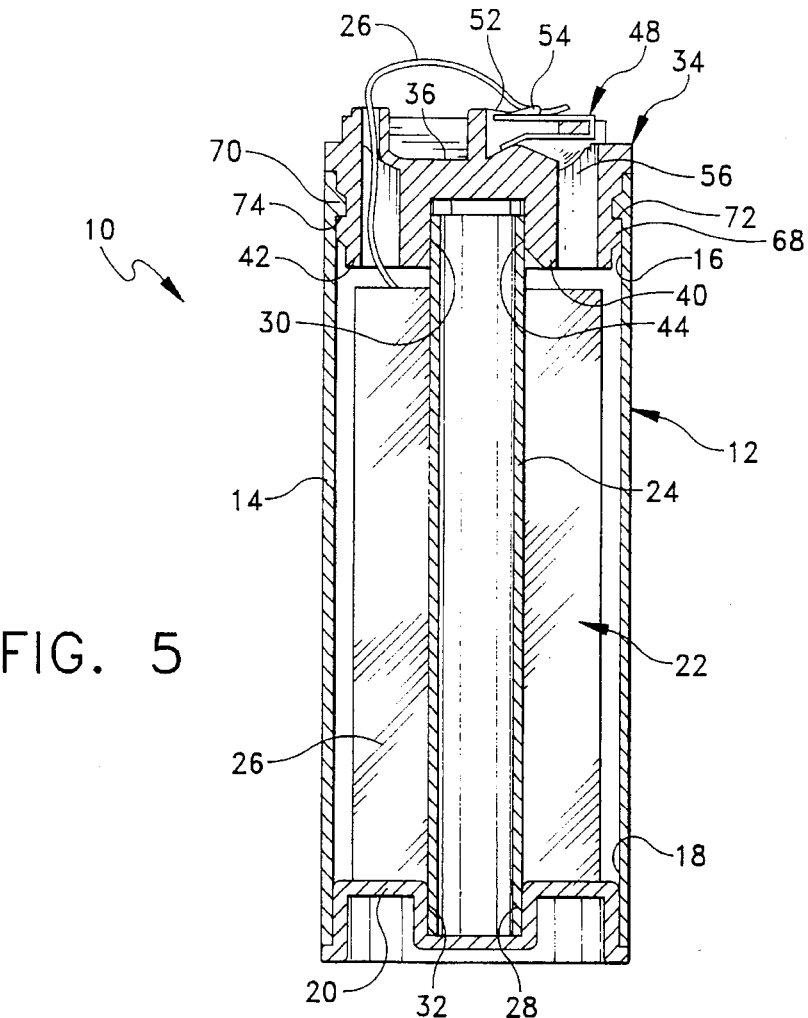
FIG. 5 is a cross-sectional view taken along line 5—5 of FIG. 3.
Figure 6:
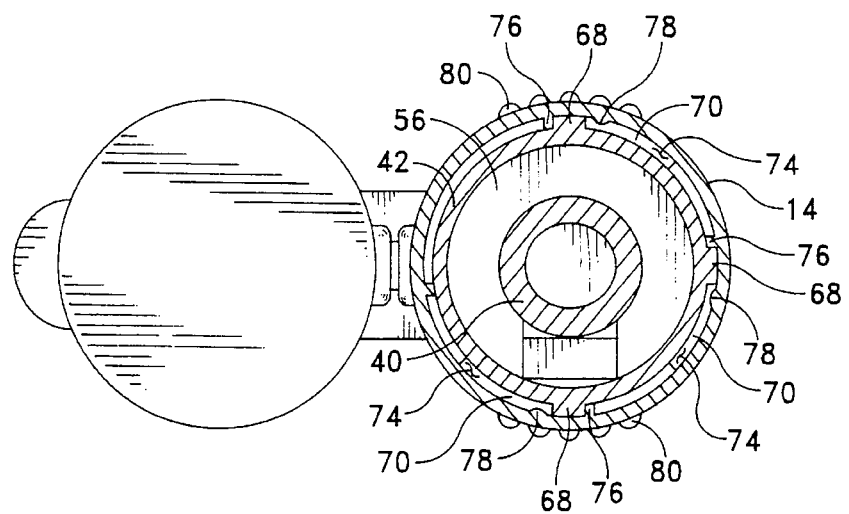
FIG. 6 is a cross-sectional view taken along line 6—6 of FIG. 4.

More specifically, the first engagement member 64 of the cap 34 comprises three radially outwardly extending, circumferential protrusions each indicated at 68 which are formed on the outer annular wall (portion) 42 of the cap 34. Similarly, the second engagement member 66 comprises three mating radially inwardly extending, circumferential protrusions each indicated at 70 formed on the inner surface of the cylindrical wall 14 of the case 12. As illustrated in FIGS. 4 and 5, the protrusions 68 of the cap 34 are shorter in length than the protrusions 70 of the case 12, and are positioned to engage the protrusions 70 of the case 12 when attaching the cap 34 to the case 12. As shown in FIG. 6, the protrusions 68, 70 may be located at the twelve, three and six o'clock positions. Each protrusion 68 of the cap 34 has an engaging surface 72 which faces its respective mating engaging surface 74 of the protrusion 70 of the case 12 when in the position illustrated in FIG. 4.

Referring to FIG. 7, the engaging member 66 of the case 12 further comprises three stop posts 76, one for each protrusion 70, formed on the inner surface of the wall 14 of the case 12. Each stop post 76 extends radially inwardly and in a direction generally transverse to the direction of its respective protrusion 70 for engaging its respective protrusion 68 of the cap 34 when rotating the cap to its attached position. The stop posts 76 are provided for defining a limit when rotating the cap 34. Also provided, for each stop post 76 and protrusion 70, is an interposed detent element 78 which extends radially inwardly a shorter distance than the stop post 76 and in a direction parallel to the direction of the stop post 76. The detent elements 78 prevent the cap 34 from inadvertently loosening and from becoming removed from the case 12.

As illustrated throughout the drawings, the outer edge of the arcuate wall 36 of the cap is serrated at 80 to assist the user of the dispenser 10 in attaching and removing the cap 34 from the case. There are two oppositely positioned serrated edges 80 so that the user may grasp the cap 34 with their thumb and forefinger when rotating the cap.

In order to assemble the floss dispenser 10, the end plug 20 is press fit into the second open end 18 of the cylindrical wall 14 in a position where it is permanently or substantially permanently attached thereto. The clip 50 of the cutting blade assembly 48 is inserted into the slot 52 provided in the arcuate wall 36 of the cap 34. The spool 22 is suitably positioned within the case 12. The cap 34 is then lowered so that it enters the first open end 16 of the cylindrical wall 14 such that the protrusions 68 of the cap 34 are adjacent the protrusions 70 of the case 12. The cap 34 is then rotated such that the engaging surfaces 72 of the protrusions 68 of the cap 34 are in engagement with respective engaging surfaces 74 of the protrusions 70 of the case 12. The cap 34 is rotated until the protrusions 68 engage their respective stop posts 76. The detent elements 78 assist in preventing the protrusions 68 of the cap 34 from backing out of engagement with the protrusions 70 of the case 12. Preferably, the cap 34 is oriented such that when the lid 58 is moved from its closed position to its open position, a logo or other printed indicia is centered with the cap 34.

Although a few exemplary embodiments of the present invention have been described in detail above, those skilled in the art readily appreciate that many modifications are possible without materially departing from the novel teachings and advantages which are described herein. Accordingly, all such modifications are intended to be included within the scope of the present invention, as defined by the following claims.

Having described the invention, what is claimed is:

1. In a floss dispenser comprising:

an essentially cylindrical case, the case including a cylindrical wall with an inner surface and two opposite ends, said case having an opening formed in at least one end;

a spool having floss wrapped around a hub, the spool being inserted into the case through said opening in its end with the hub of the spool mounted parallel to the length of the case; and a cap received by the opening in the end of the case, said cap having an outer circumferential wall portion, means for receiving and centering the hub of the spool when the cap is sealing the opening of the case, and at least one opening therein through which floss is threaded out of the end of the case;

wherein the improvement comprises means for securely attaching the cap to the case, said cap securing means having a first interlocking engagement member associated with the cap and a mating second interlocking engagement member associated with the case, said first engagement member being defined by at least one radially outwardly extending, circumferential protrusion formed on the wall portion of the cap, and said second engagement member being defined by at least one radially inwardly extending, circumferential protrusion formed on the inner surface of the cylindrical wall of the case, wherein said second engagement member of the case includes a stop post formed on the inner wall of the case, said stop post extending radially inwardly and in a direction generally transverse to the direction of the second circumferential protrusion of the cylindrical wall of the case, said stop post engaging the first circumferential protrusion of the cap when rotating the cap to its attached position and defining a limit for rotating the cap, the arrangement being such that upon insertion of the cap into the open end of the case and rotating the cap, said first engagement member of the cap engages the second engagement member of the case.

2. The floss dispenser as set forth in claim 1, wherein said protrusion of the cap has an engaging surface which faces a mating engaging surface of the protrusion of the case when in engagement therewith.

3. The floss dispenser as set forth in claim 1, wherein said second engagement member of the case further comprises an interposed detent element which extends radially inwardly and in a direction generally parallel to the stop post.

4. The floss dispenser as set forth in claim 1, wherein said first engagement member comprises two additional radially outwardly extending, circumferential protrusions formed on the wall portion of the cap, and said second engagement member comprises two additional mating radially inwardly extending, circumferential protrusions formed on the inner surface of the cylindrical wall of the case, the arrangement being such that the three protrusions of the cap engage their respective three protrusions of the case when attaching the cap to the case.

5. The floss dispenser as set forth in claim 1, wherein said cap, when engaged with the case, is oriented in a predetermined position with respect to indicia printed on the case.

6. A cap for a floss dispenser of the type comprising an essentially cylindrical case, said cap having an outer circumferential wall portion, the case including a cylindrical wall with an inner surface and two opposite ends, said case having an opening formed in at least one end, and a spool having floss wrapped around a hub, the spool being inserted into the case through said opening in its end with the hub of the spool mounted parallel to the length of the case, said cap being received within the opening in the end of the case and comprising:

means for receiving and centering the hub of the spool when the cap is sealing the opening of the case;

at least one opening therein through which floss is threaded out of the end of the case; and means for securely attaching the cap to the case comprising a first interlocking engagement member associated with the cap and a mating second interlocking engagement member associated with the case, said first engagement member having at least one radially outwardly extending, circumferential protrusion formed on the wall portion of the cap, and said second engagement member having at least one radially inwardly extending, circumferential protrusion formed on the inner surface of the cylindrical wall of the case, said protrusion of the cap engaging the protrusion of the case when attaching the cap to the case, said second engagement member of the case having a stop post formed on the inner wall of the case, said stop post extending radially inwardly and in a direction generally transverse to the direction of the second circumferential protrusion of the cylindrical wall of the case, said stop post engaging the first circumferential protrusion of the cap when rotating the cap to its attached position and defining a limit for rotating the cap, the arrangement being such that upon insertion of the cap into the open end of the case and rotating the cap, the first engagement member of the cap engages the second engagement member of the case.

7. The cap as set forth in claim 6, wherein said protrusion of the cap has an engaging surface which faces a mating engaging surface of the protrusion of the case when in engagement therewith.

8. The cap as set forth in claim 6, wherein said second engagement member of the case further comprises an interposed detent element which extends radially inwardly and in a direction generally parallel to the stop post.

9. The cap as set forth in claim 6, wherein said first engagement member comprises two additional radially outwardly extending, circumferential protrusions formed on the wall portion of the cap, and said second engagement member comprises two additional mating radially inwardly extending, circumferential protrusions formed on the inner surface of the cylindrical wall of the case, the arrangement being such that the three protrusions of the cap engage their respective three protrusions of the case when attaching the cap to the case.

10. The cap as set forth in claim 6, wherein said cap, when engaged with the case, is oriented in a predetermined position with respect to indicia printed on the case.

* * * * *